(12) United States Patent
Cohen et al.

(10) Patent No.: US 10,806,789 B2
(45) Date of Patent: Oct. 20, 2020

(54) COMPOSITION FOR ENHANCED ABSORPTION OF SUPPLEMENTS

(71) Applicant: The LIV Group Inc., Marina del Rey, CA (US)

(72) Inventors: Brandin Besore Cohen, Playa Vista, CA (US); Hayden Andrew Fulstone, Santa Monica, CA (US)

(73) Assignee: The LIV Group Inc., El Segundo, CA (US)

( * ) Notice: Subject to any disclaimer, the term of this patent is extended or adjusted under 35 U.S.C. 154(b) by 226 days.

(21) Appl. No.: 15/925,644

(22) Filed: Mar. 19, 2018

(65) Prior Publication Data

US 2018/0326064 A1 Nov. 15, 2018

Related U.S. Application Data

(60) Provisional application No. 62/607,844, filed on Dec. 19, 2017, provisional application No. 62/505,800, filed on May 12, 2017.

(51) Int. Cl.

| | | |
|---|---|---|
| *A61K 47/02* | (2006.01) |
| *A61K 47/12* | (2006.01) |
| *A61K 31/4045* | (2006.01) |
| *A23L 33/105* | (2016.01) |
| *A61K 31/16* | (2006.01) |
| *A61K 36/84* | (2006.01) |
| *A23L 33/16* | (2016.01) |
| *A61K 31/405* | (2006.01) |
| *A61K 9/127* | (2006.01) |
| *A23L 33/15* | (2016.01) |
| *A61P 25/00* | (2006.01) |
| *A23L 33/125* | (2016.01) |
| *A61K 9/00* | (2006.01) |

(52) U.S. Cl.
CPC ............ *A61K 47/02* (2013.01); *A23L 33/105* (2016.08); *A23L 33/125* (2016.08); *A23L 33/15* (2016.08); *A23L 33/16* (2016.08); *A61K 9/0014* (2013.01); *A61K 9/0021* (2013.01); *A61K 9/127* (2013.01); *A61K 31/16* (2013.01); *A61K 31/405* (2013.01); *A61K 31/4045* (2013.01); *A61K 36/84* (2013.01); *A61K 47/12* (2013.01); *A61P 25/00* (2018.01); *A23V 2002/00* (2013.01)

(58) Field of Classification Search
CPC ............ A23V 2002/00; A23V 2200/33; A23V 2250/032; A23V 2250/16; A23V 2250/1614; A23V 2250/1628; A23V 2250/214; A23V 2250/258; A23V 2250/5114; A23V 2250/61; A23V 2250/628; A23V 2250/7046; A23V 2250/705; A23V 2250/7052; A23V 2250/706; A23V 2250/708; A23L 33/105; A23L 33/125; A23L 33/15; A23L 33/16; A61K 31/4045; A61K 31/405; A61K 36/84; A61K 47/02; A61K 47/12; A61K 9/0014; A61K 9/0021; A61K 9/127; A61K 31/198; A61K 36/185; A61P 25/00

See application file for complete search history.

(56) References Cited

U.S. PATENT DOCUMENTS

| | | |
|---|---|---|
| 5,397,786 A | 3/1995 | Simone |
| 7,160,565 B2 | 1/2007 | Rifkin |
| 7,566,463 B2 | 7/2009 | Ayala |
| 2001/0014338 A1 | 8/2001 | Cefali |
| 2003/0194448 A1 | 10/2003 | Mitchell et al. |
| 2005/0008685 A1 | 1/2005 | Mitchell et al. |
| 2005/0095320 A1 | 5/2005 | Bolted et al. |
| 2008/0299199 A1 | 12/2008 | Bar-Shalom et al. |
| 2010/0120887 A1 | 5/2010 | Terman et al. |
| 2011/0142962 A1 | 6/2011 | Luebbers et al. |
| 2011/0212198 A1 | 9/2011 | Vermeulen et al. |
| 2013/0004594 A1 | 1/2013 | Dolhun |
| 2014/0113939 A1 | 4/2014 | Cefali et al. |
| 2014/0370145 A1 | 12/2014 | Friesen et al. |
| 2016/0038596 A1 | 2/2016 | Wright et al. |
| 2016/0199410 A1 | 7/2016 | Hurt et al. |

OTHER PUBLICATIONS

"Low-osmolarity Oral Rehydration Salts (ORS)," retrieved 2017 at <<https://rehydrate.org/ors/low-osmolarity-ors.htm>>, World Health Organization, Apr. 23, 2014, 9 pages.
"Oral Rehydration Salts: Production of the new ORS," World Health Organization and Unicef, 2006, 123 pgs.
"Who Drug Information," Who Drug Information, World Health Organization, vol. 16, No. 2, 2002, pp. 113-203.
Fordtran, et al., "The Mechanisms of Sodium Absorption in the Human Small Intestine," J. Clin. Invest., vol. 47, No. 4, 1968, pp. 884-900.

(Continued)

*Primary Examiner* — Aaron J Kosar
(74) *Attorney, Agent, or Firm* — Lee & Hayes, P.C.; Tanya M. Harding (57) ABSTRACT

A composition that includes at least one target supplement and at least one rehydration formulation is described. When the at least one target supplement is ingested as part of the composition, the bioavailability of at least one target supplement is enhanced as compared to when it is ingested separate from the composition. The at least one target supplement is absorbed more quickly and in a greater amount when it is ingested as part of the composition than when it is ingested separate from the composition. The composition also hydrates a subject more quickly.

22 Claims, 2 Drawing Sheets

(56) References Cited

OTHER PUBLICATIONS

Kelly & Nadeau, "Oral Rehydration Solution: A Low-Tech Oft Neglected Therapy," Practical Gastroenterology, vol. 21, 2004, pp. 51-62.
Ruxin, Joshua Nalibow, "Magic Bullet: The History of Oral Rehydration Therapy," Medical History, vol. 38, 1994, pp. 363-397.
Kalman & Lepeley, "A Review of Hydration," Strength and Conditioning Journal, vol. 32, No. 2, 2010, pp. 56-63.
The PCT Search Report and Written Opinion, dated Aug. 8, 2018, for PCT Application No. PCT/US18/32472, 10 pages.

COMPOSITION FOR ENHANCED ABSORPTION OF SUPPLEMENTS

RELATED APPLICATIONS

This Application claims priority to U.S. Provisional Application No. 62/607,844, filed Dec. 19, 2017, and U.S. Provisional Application No. 62/505,800, filed May 12, 2017, the entire contents of which are incorporated herein by reference.

BACKGROUND

There is a wide range of supplements available to drink or eat in over-the-counter form. These supplements are used in attempts to achieve various ends. For example, a person may use supplements in an effort to fall asleep, to supplement nutrition, to provide increased energy, etc.

Typically, such supplements are taken orally. Though absorption of supplements, such as vitamins and minerals, can take place anywhere along the digestive tract, the small intestine is the main portion of the digestive tract in which such absorption occurs. The nutrients are absorbed into the bloodstream in the small intestine via a diffusion process.

Thus, supplements taken by mouth must travel down a substantial portion of the digestive tract, and then must be absorbed by the body. Therefore, it can take a long time to feel the supplements' effects. Often, supplements must be ingested hours before the time of the effect sought to be obtained from them. This delay can cause difficulties such as frustration, non-compliance with recommendations to take the supplements, and/or taking more than the recommended dosage in the hopes of seeing an effect sooner.

Therefore, there is a demand for a means to enhance the bioavailability of supplements, and to enable their effects to be felt sooner.

SUMMARY

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter.

This disclosure describes a composition, methods of making the composition, and methods of using the composition. The composition, in an embodiment, includes but is not limited to at least one rehydration formulation and at least one target supplement that targets a condition of a subject, wherein the target supplement has enhanced bioavailability when ingested by a subject in need thereof as part of the composition as compared to when the target supplement is ingested separately from the composition.

BRIEF DESCRIPTION OF THE DRAWINGS

The detailed description that follows is described with reference to non-limiting and non-exhaustive embodiments shown in the accompanying figures. In the figures, the left-most digit(s) of a reference number identifies the figure in which the reference number first appears. The same reference numbers in different figures indicate similar or identical items.

DETAILED DESCRIPTION

Overview

The following description sets forth specific embodiments of a composition for enhanced absorption of target supplements that incorporates elements recited in the appended claims and related methods of making and using such compositions. The embodiments are described with specificity in order to meet statutory requirements. However, the description itself is not intended to limit the scope of this patent. Rather, the inventors have contemplated that the claimed invention might also be embodied in other ways, to include different elements or combinations of elements similar to the ones described in this document, in conjunction with other present or future technologies.

As noted above, this disclosure describes a composition, methods of making the composition, and methods of using the composition. The composition is generally comprised of at least one rehydration formulation and at least one target supplement that targets a condition of a subject, wherein the target supplement has enhanced bioavailability when ingested by the subject in need thereof as part of the composition as compared to when the target supplement is ingested separately from the composition. As used herein, a "subject" means any mammal, e.g., a human mammal or a non-human mammal (e.g., a primate). As used herein, a "target supplement" is a product taken orally by a subject that contains at least one ingredient that is intended to target a condition of a subject.

The composition may optionally contain additional ingredients including, but not limited to, flavors, sweeteners, colorants, preservatives, anti-caking agents, gelling agents, antimicrobials, citric acid, or excipients.

Each of the at least one rehydration formulation, the at least one target supplement, and the optional additional ingredients will be discussed below.

The rehydration formulation portion of the composition may contain at least five components: sodium, chloride, glucose-containing saccharide, potassium, and citrate.

Sodium ions are one component of the rehydration formulation described herein. In general, rehydration formulations contain sodium at least in order to prevent hyponatremia that would otherwise result from diluting the blood with a large amount of water. Additionally, sodium may be lost during vomiting or diarrhea. Sodium may be included in the rehydration formulation in the form of cations of salts, which can include, but are not limited to, sodium chloride, monosodium phosphate, disodium phosphate, trisodium phosphate, sodium citrates (including trisodium citrate), sodium carbonate, sodium bicarbonate, sodium lactate, sodium gluconate, tetrasodium acid pyrophosphate, sodium acid sulfate, or sodium hydroxide.

The sodium, in an example of a rehydration formulation described herein, is in the form of sodium chloride and sodium citrate.

In an example, the sodium chloride has an osmolarity of about 35 mmol/L to about 40 mmol/L, or about 37 mmol/L to about 43 mmol/L, or about 40 mmol/L to about 42 mmol/L, or the sodium chloride has a weight of about 2.0 g/L to about 2.3 g/L, or about 2.2 g/L to about 2.5 g/L, or about 2.3 to about 2.5 g/L. As used herein, "osmolarity" is the concentration of a solution expressed as the total number of solute particles per liter. Osmolarity may also be expressed in units of milliequivalents per liter (meq/L), where 1 meq is equal to 1 mmol of a solute in a solution. In contrast, "osmolality" is the concentration of a solution expressed as the total number of solute particles per kilogram.

In an example, the sodium citrate in a rehydration formulation described herein has an osmolarity of about 10 mmol/L to about 15 mmol/L, about 7.0 mmol/L to about 13 mmol/L, or about 8.0 mmol/L to about 10 mmol/L, or has a weight of about 0.98 g/L to about 1.5 g/L, or about 0.69 g/L to about 1.3 g/L, or about 0.78 g/L to about 0.98 g/L, or about 2.0 g/L to about 3.0 g/L.

Another component of the at least one rehydration formulation is a glucose-containing saccharide. As used herein, a "glucose-containing saccharide" means either glucose, or a saccharide that can be hydrolyzed to form a composition containing glucose (e.g., glucose, sucrose, dextrose, lactose, maltose, amylase, glycogen, maltodextrin, etc.). For example, gastric acidity converts sucrose to glucose and fructose during digestion. Reference to any saccharide by a single name also includes all forms of that saccharide which may be in equilibrium with the specific saccharide named, in aqueous mixture at room temperature.

An osmolarity of 50 mmol/L of glucose may increase water absorption of water and sodium in the small intestine of a human subject by 4 to 6 times in the jejunum (the middle portion of the small intestine) and 2 to 3 times in the ileum (the distal portion of the small intestine). The glucose in an example has an osmolarity of about 50 mmol/L to about 60 mmol/L, about 50 mmol/L to about 70 mmol/L, or about 45 mmol/L to about 80 mmol/L.

In an example, the glucose-containing saccharides included in the rehydration formulation include at least glucose and sucrose. In an example, glucose is added at a weight of about 8.1 g/L to about 14.4 g/L, about 9.0 g/L to about 12.6 g/L, or about 9.0 to about 10.8 g/L, and sucrose is added at a weight of about 12.6 g/L to about 15.7 g/L, or about 12.9 g/L to about 14.8 g/L, or about 13.2 g/L to about 13.8 g/L.

In another example, dextrose and sucrose are included in the rehydration formulation as the glucose-containing saccharides. Dextrose is a form of glucose.

In another example, glucose is the glucose-containing saccharide included in the rehydration formulation. In an example, glucose is added at a weight of about 14.5 g/L to about 15.0 g/L, about 14.0 g/L to about 15.6 g/L, or about 12.8 g/L to about 16.8 g/L.

In yet another example, dextrose is the glucose-containing saccharide included in the rehydration formulation. In an example, dextrose is added at a weight of about 14.5 g/L to about 15.0 g/L, about 14.0 g/L to about 15.6 g/L, or about 12.8 g/L to about 16.8 g/L.

In an embodiment, the at least one rehydration formula described herein contains a molar ratio of approximately 1:1 glucose to sodium. An approximately equal amount (in osmolarity) of both sodium and glucose optimizes the glucose-sodium active transport mechanism.

In an example, chloride and citrate are two other components of the rehydration formulation.

Chloride and citrate ions may help prevent electrolyte imbalance. Chloride may be included in the rehydration formulation in the form of an anion of a salt. Chloride-containing ingredients may include, but are not limited to, sodium chloride, potassium chloride, calcium chloride, and magnesium chloride.

In an example, chloride is present in the form of sodium chloride, in the amounts listed above for purposes of sodium inclusion. In another example, chloride is present in the form of potassium chloride, with a weight of about 1.50 g/L to about 1.66 g/L, or of about 1.28 g/L to about 1.88 g/L, or of about 1.0 g/L to about 2.0 g/L.

Meanwhile, citrate may be included in the rehydration formulation. In an example, the citrate is in the form of sodium and/or potassium citrate salts (e.g., trisodium citrate, sodium citrate (dehydrate), potassium citrate). Citrate may also be present as citric acid or as a citric ester (e.g., triethyl citrate) that can be hydrolyzed into citric acid or citrate ion.

In an example, citrate is present in the form of sodium citrate in the amount listed above for purposes of sodium inclusion, and in the form of potassium citrate, with a weight of about 1.3 g/L to about 1.7 g/L, or about 1.4 g/L to about 1.6 g/L.

In another example, citrate is present in the form of sodium citrate, with a weight of about 0.98 g/L to about 1.5 g/L, or about 0.69 g/L to about 1.3 g/L, or about 0.78 g/L to about 0.98 g/L, or about 2.0 g/L to about 3.0 g/L. In an example, another component of the rehydration formulation described herein is potassium. Potassium may be included in a rehydration formulation because, as with sodium, vomiting and diarrhea may lead to substantial loss of potassium that needs to be replaced. Also, as with sodium, the potassium may be present as a cation of a salt. Potassium salts include but are not limited to potassium chloride, potassium phosphate, potassium citrate, potassium carbonate, potassium bicarbonate, and potassium hydroxide.

In an example, potassium is present in the form of potassium citrate in the weights listed above for purposes of citrate inclusion in the rehydration formulation, and in the form of dipotassium phosphate, with a weight of about 0.3 g/L to about 0.9 g/L, or of about 0.5 g/L to about 0.7 g/L.

In another example, potassium is present in the form of potassium chloride, with a weight of about 1.50 g/L to about 1.66 g/L, or of about 1.28 g/L to about 1.88 g/L, or of about 1.0 g/L to about 2.0 g/L.

Additionally, the rehydration formulation described herein (once diluted to the proper concentration described above and when the optional additional ingredients (described below) are added) has a total osmolarity that falls within at least one of the standard or "reduced osmolarity ORS" ranges recommended by WHO and UNICEF (200 to 310 mmol/L and 210 to 260 mmol/L, respectively). See *WHO Drug Information* Vol. 16, No. 2, 2002, "New formula oral rehydration salts," available online at apps.who.int/medicinedocs/en/d/Js4950e/2.4.html. See also "Oral Rehydration Salts (ORS) A New Reduced Osmolarity Formulation," available online at rehydrate.org/ors/who-unicef-statement.html (May 10, 2002).

The rehydration formulation as described herein is believed to exploit the glucose-sodium active transport mechanism to enhance absorption of water and target supplements into the bloodstream. In the small intestine, sodium passes into intestinal epithelial cells via co-transport with glucose by way of the SGLT1 protein. Two sodium ions and one molecule of glucose are transported together across the epithelial cell membrane to the bloodstream via the SGLT1 protein. The absorption of glucose and sodium out of the small intestine creates an osmotic force. For each transport cycle, water molecules move into the epithelial cells to maintain osmotic equilibrium. Water that is absorbed from the lumen of the small intestine rather than being excreted is available for systemic distribution by the bloodstream for cellular hydration. Hydration is thus delivered to the bloodstream faster and in larger quantities with the rehydration formula than by drinking water alone. In an embodiment of a rehydration formula according to the instant disclosure, the relative quantities of the components in the rehydration formulation may be in amounts as described herein.

As noted above, the composition described herein, in an embodiment, includes at least one rehydration formulation, described above, and also at least one target supplement that targets a condition of a subject. When ingested by a subject in need thereof, the rate of absorption of the target supplement when part of the composition that includes the rehydration formulation (the "second absorption rate") is faster than the rate of absorption of the target supplement when ingested separately from the composition (the "first absorption rate"). In an embodiment, the second absorption rate may be about 10% to about 600% faster than when the target supplement is absorbed by means other than the herein described composition. For example, the second absorption rate may be about 1.1 times to about 6 times faster than the first absorption rate, or about 2 times to about 6 times faster, or about 2 times to about 3 times faster. Additionally, a larger quantity of the target supplement is absorbed when part of the composition than when ingested separately from it.

For at least these reasons, the bioavailability of the target supplement is enhanced when ingested as part of the composition. Additionally, the composition described herein rehydrates a subject more quickly and efficiently than water alone.

In an embodiment, depending on the condition that is being targeted, more than one target supplement may be included in the composition.

Generally, example conditions of a subject that are targeted with a target supplement include but are not limited to sleeplessness, sleepiness, sluggishness, post-exercise fatigue, anticipated post-exercise fatigue, electrolyte deficiency, low energy, protein deficiency, vitamin deficiency, compromised immunity, joint pain, overweight, muscle loss or weakness, inflammation, mood instability, depression, poor concentration, poor memory, pain, jet lag, etc.

Generally, examples of the types of target supplements that may be included in an example composition described herein include, but are not limited to, vitamins, minerals, amino acids, amino acid analogues, caffeine, proteins, herbal/botanical/plant supplements, nutraceuticals, probiotics, prebiotics, soluble fiber, insoluble fiber, anti-oxidants, glucosamine, glycosaminoglycans, hormones, etc. Each target supplement is suitable for dissolving in water.

Examples of vitamins that may be included in the composition described herein include, but are not limited to, vitamin $B_1$, vitamin $B_2$, vitamin $B_6$, vitamin $B_{12}$, folic acid (vitamin $B_9$), niacin (vitamin $B_3$), pantothenic acid (vitamin $B_5$), biotin (vitamin $B_7$), vitamin C, vitamin $D_3$, vitamin E, vitamin A, and vitamin K.

Examples of minerals that may be included in the composition described herein include, but are not limited to, zinc, copper, manganese, nickel, tin, silicon, magnesium, molybdenum, selenium, chromium, vanadium, boron, calcium, iron, iodine, and phosphorus.

Examples of amino acids that may be included in the composition described herein include, but are not limited to, branched chain amino acids ("BCAAs"), gamma-aminobutyric acid ("GABA"), L-arginine, L-carnitine, acetyl L-carnitine, glutamine, L-lysine, L-tyrosine, taurine, L-cysteine, L-tryptophan, L-theanine, L-carnosine, L-leucine, L-isoleucine, L-valine, beta-alanine, and 5-hydroxytryptophan ("5-HTP").

Examples of anti-oxidants that may be included in the composition described herein include, but are not limited to, carotene, eugenol, lutein, and lycopene.

Examples of herbal/botanical/plant supplements that may be included in the composition described herein include, but are not limited to, valerian, chamomile, passionflower, yerba mate, ginger, carrot, or *Echinacea*.

An example of a hormone that may be included in the composition described herein is, but is not limited to, melatonin.

Examples of probiotics that may be included in the composition described herein include, but are not limited to, *Lactobacillus reuteri, Lactobacillus acidophilus*, and *Bifidobacterium bifidum*.

The target supplement may be part of—and ingested as part of—the composition. As described above, the rehydration formulation, ingested by itself, results in water and sodium being pulled across the small intestine wall and into the bloodstream more quickly, and in larger quantities, due to the action of the glucose-sodium transport system. The target supplement is absorbed more quickly, and in larger quantities, when ingested as part of the composition than when ingested separately from it. In an embodiment, the absorption rate of the target supplement when part of the composition may be about faster than when the target supplement is absorbed by means other than the herein described composition. For example, about 1.1 times to about 6 times faster, or about 2 times to about 6 times faster, or about 2 times to about 3 times faster. For at least these reasons, the target supplement, when part of the composition, has enhanced bioavailability while in the composition as compared to when ingested apart from the composition.

In certain embodiments, the target supplement itself may be a raw ingredient of the composition. In other embodiments, the target supplement may be a part of another ingredient. For example, vitamin C may be added directly in its raw form or may be contained as part of spinach powder. As another example, protein may be included as the target supplement as protein powder or as soy or whey. Either the raw or "bulk" substance is referred to as a "target supplement" herein.

As noted above, at least one target supplement is included in the composition. The selection of the at least one target supplement may be determined by the condition that is being targeted in a subject.

In an example, the condition being targeted may be sleeplessness, and at least one of the following target supplements may be included in the composition: melatonin, 5-HTP, valerian root, L-theanine, chamomile, L-tryptophan, vitamin C, algae, passionflower, zinc, calcium, or magnesium.

In another example, the condition may be electrolyte depletion (for example, as might occur during exercise) and the composition may include at least one of the following target supplements: sodium, potassium, phosphorus, magnesium, selenium, calcium, manganese, or zinc.

In yet another example, the condition may be low energy. In an embodiment, the composition may include at least one of the following target supplements: yerba mate, vitamins (for example, vitamin $B_2$, $B_{12}$, niacin, a B-complex vitamin, or vitamin D), caffeine, coffee beans, green coffee extract, matcha green tea, black tea, white tea, mushrooms (for example, reishi or cordyceps), ginseng, ashwagandha, or theobromine.

In still another example, the condition may be compromised immunity, and the composition may include at least one of the following target supplements: vitamin C, zinc, *Echinacea*, carrot, or ginger.

In a further example, the condition may be protein deficiency, and the composition may include at least one of the following target supplements: wheat or soy.

In yet a further example, the condition may be exercise-related joint pain or inflammation and the composition may include at least the following target supplement: glucosamine.

In a still further example, the condition may be pre-exercise preparation or anticipated post-exercise fatigue, and the composition may include at least one of the following target supplements: caffeine, BCAAs, beta-alanine, L-arginine, L-citrulline, or beetroot.

In another example, the condition may be post-exercise fatigue, and the composition may include at least one of the following target supplements: whey protein, soy protein, BCAAs, glutamine, beta-alanine, or creatine.

In a yet further example, the condition may be vitamin deficiency, and the composition may include at least one of the following target supplements: vitamin $B_1$, vitamin $B_2$, vitamin $B_6$, vitamin $B_{12}$, folic acid (vitamin $B_9$), niacin (vitamin $B_3$), pantothenic acid (vitamin $B_5$), biotin (vitamin $B_7$), vitamin C, vitamin $D_3$, vitamin E, vitamin A, and vitamin K, either individually or in combination form. For example, the condition may be vitamin deficiency, and the composition may include at least one of vitamin C, vitamin B3, vitamin B5, vitamin B6, and vitamin B12.

Other conditions may be targeted by the composition described herein, and other target supplements may be used to treat the listed conditions and other conditions.

In addition to the at least one rehydration formulation and the at least one target supplement, the composition, in an embodiment, may also contain optional additional ingredients, which may include at least one of natural flavors, artificial flavors, sweeteners (e.g., sodium saccharine, aspartame, acesulfame-K, chlorinated sucrose, erythritol and/or rebaudioside), colorants, preservatives (e.g., potassium sorbate, sodium benzoate), excipients (e.g., silica, cellulose, cellulose esters, polyethylene glycol, and lecithin), anti-caking agents, gelling agents, antimicrobials (e.g., germacrenes), citric acid, or any combination thereof.

Table 1 shows the quantities of ingredients in an embodiment of a composition described herein, in both weight and osmolarity, when dissolved in 1.0 liter of water. For purposes of this application, 1.0 liter of water is presumed to weigh 1.0 kg.

TABLE 1

| Ingredient | Weight (grams) | Weight (g/kg/solv) | Molecular mass | Osmolarity (mMol/L) |
|---|---|---|---|---|
| Sugar (sucrose) | 6.40 | 13.5278 | 342.29 | 39.52 |
| glucose | 4.56 | 9.6386 | 180.15 | 53.50 |
| citric acid | 1.78 | 3.7540 | 192.124 | 19.54 |
| sodium chloride | 0.96 | 2.0292 | 58.44 | 34.72 |
| potassium citrate | 0.69 | 1.4678 | 324.41 | 4.52 |
| sodium citrate | 0.54 | 1.1499 | 294.1 | 3.91 |
| Citral | 0.21 | 0.4397 | 152.24 | 2.89 |
| germacrene | 0.21 | 0.4397 | 204.35 | 2.15 |
| dipotassium phosphate | 0.27 | 0.5749 | 174.2 | 3.30 |
| silicon dioxide | 0.14 | 0.3044 | 68.08 | 5.07 |
| rebaudioside A | 0.10 | 0.2198 | 967.01 | 0.23 |
| vitamin C | 0.07 | 0.1522 | 176.12 | 0.86 |
| Niaciniamide (vitamin B3) | 0.02 | 0.0511 | 122.13 | 0.42 |
| D-calcium Panthothenate (vitamin B5) | 0.01 | 0.0255 | 476.53 | 0.05 |
| pyridoxine hydrochloride (vitamin B6) | 0.00 | 0.0051 | 205.64 | 0.02 |

TABLE 1-continued

| Ingredient | Weight (grams) | Weight (g/kg/solv) | Molecular mass | Osmolarity (mMol/L) |
|---|---|---|---|---|
| Cayanocobalamin (vitamin B12) | 0.00 | 0.000 | 1355.37 | 0.00 |
| maltodextrin | 0.02 | 0.033 | 342.29 | 0.10 |

Table 2 shows the osmolarity of the individual components of the rehydration formulation as well as the total osmolarity of all ingredients for the composition listed in Table 1.

TABLE 2

|  | Osmolarity (mmol/liter) |
|---|---|
| Total in 17 ingredients | 227 |
| glucose | 52.3 |
| sodium | 45.4 |
| chloride | 33.9 |
| potassium | 19.7 |
| citrate | 8.2 |

Table 3 shows the quantities of ingredients in another embodiment of a composition described herein, in which the condition being targeted is sleeplessness. The quantities of the ingredients are listed in weight and in osmolarity when dissolved in 8 ounces (236.58 grams) of water. The ingredients include (1) the components of the rehydration formula, (2) the at least one target supplement, and (3) optional additional ingredients, ter. For purposes of this application, 1.0 liter of water is presumed to weigh 1.0 kg.

TABLE 3

| Ingredient | Weight (grams) | Weight (g/kg/solv) | Molecular mass | Osmolarity (mMol/L) |
|---|---|---|---|---|
| Dextrose | 3.5000 | 14.7941 | 180.15 | 81.0 |
| citric acid, anhydrous | 0.4817 | 2.0361 | 192.124 | 10.5 |
| sodium chloride | 0.5500 | 2.3248 | 58.44 | 39.2 |
| sodium citrate | 0.6000 | 2.5361 | 258.069 | 9.7 |
| silicon dioxide syloid | 0.2000 | 0.8454 | 60.08 | 13.9 |
| Fly, Nat Blue | 0.2000 | 0.8454 | 611 | 1.4 |
| Fly, Nat Lav | 0.1000 | 0.4227 | 300 | 1.4 |
| Color - Beet juice powder | 0.0400 | 0.1691 | 551 | 0.3 |
| Color - Grape Blue powder | 0.1200 | 0.5072 | 500 | 1.0 |
| Stevia extract | 0.0625 | 0.2642 | 804 | 0.3 |
| Niaciniamide (vitamin B3) | 0.0550 | 0.2325 | 122.12 | 1.9 |
| Thiamine Mononitrate | 0.0036 | 0.0152 | 327.36 | 0.0 |
| Jerusalem artichoke inulin powder | 2.4842 | 10.5005 | 4000 | 2.6 |
| Valerian extract | 0.1750 | 0.7397 | 130.187 | 5.6 |
| L-theanine | 0.0500 | 0.2113 | 174.198 | 1.2 |
| Melatonin | 0.0030 | 0.0127 | 232.278 | 0.1 |
| Potassium chloride | 0.3750 | 1.5851 | 74.551 | 21.0 |

Table 4 shows the osmolarity of the individual components of the rehydration formulation as well as the total osmolarity of all ingredients for the composition listed in Table 3.

TABLE 4

|  | Osmolarity (mmol/liter) |
|---|---|
| Total in 17 ingredients | 266 |
| dextrose | 81.0 |
| sodium | 68.3 |
| chloride | 60.2 |

TABLE 4-continued

| | Osmolarity (mmol/liter) |
|---|---|
| potassium | 21.0 |
| citrate | 9.7 |

Figure 1:
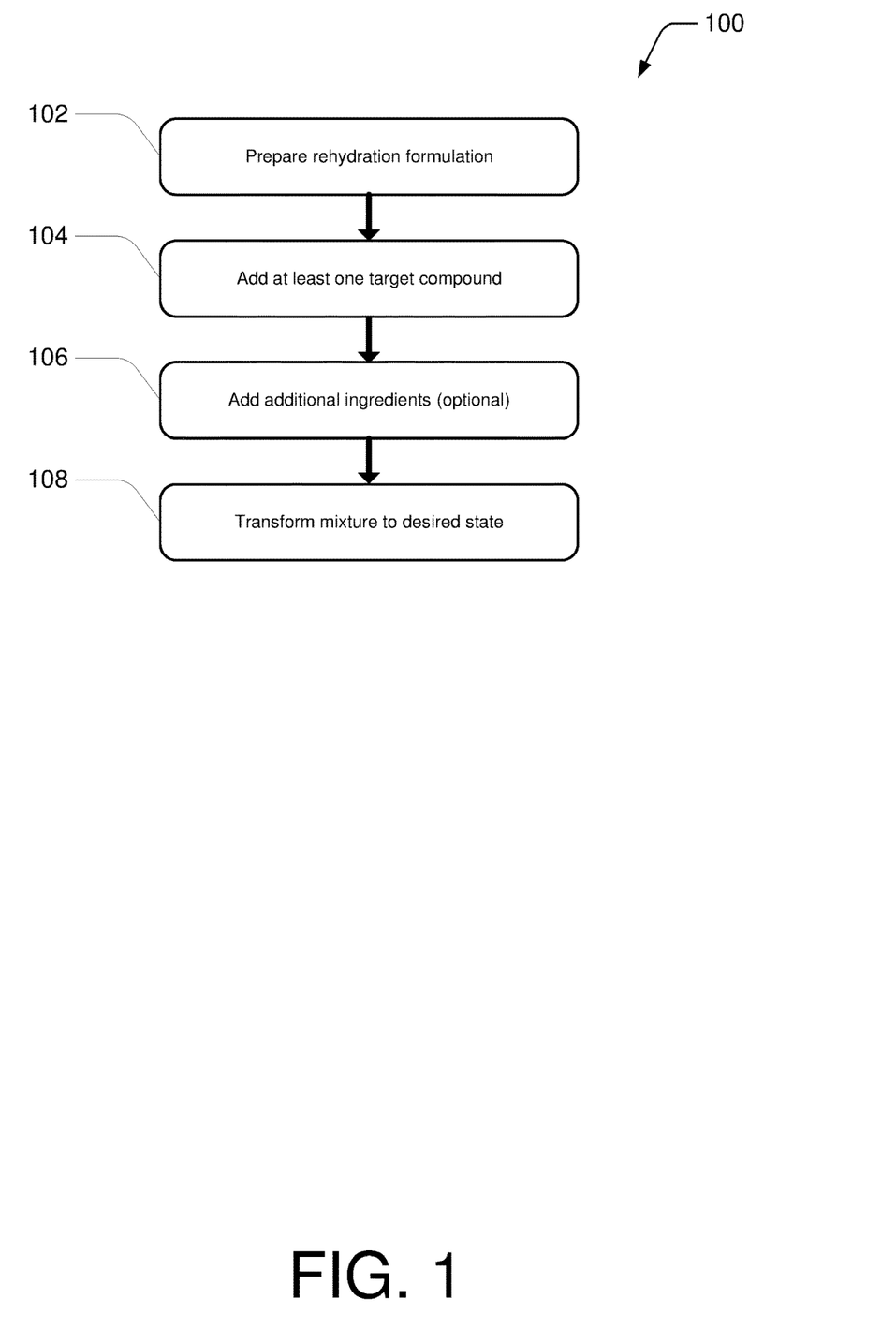
FIG. 1 is a flow diagram of an exemplary method of making a composition as described herein.
Figure 2:
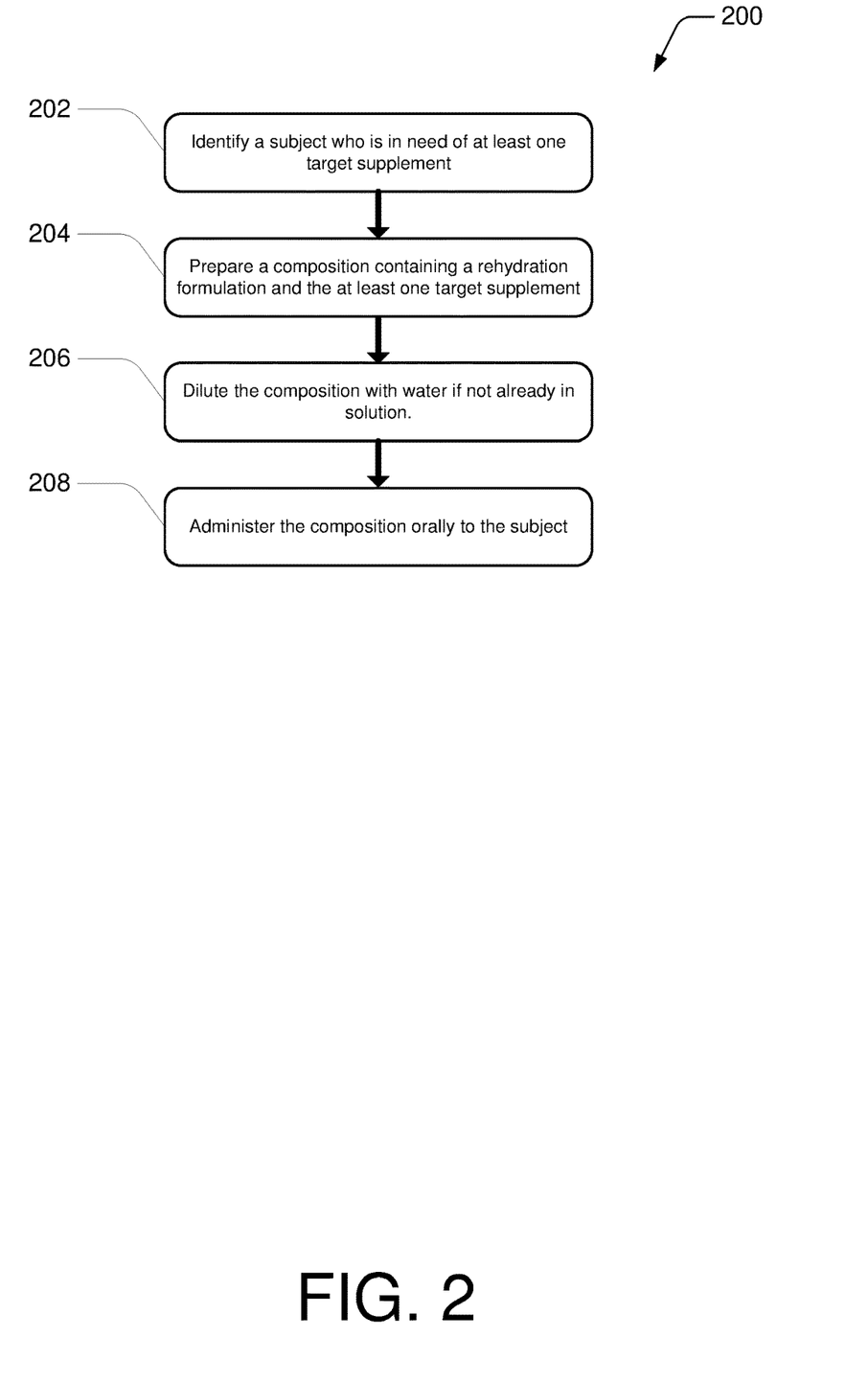
FIG. 2 is a flow diagram of an exemplary method of using a composition as described herein.

Various compositions and methods for making and using the compositions, are described further with reference to FIGS. 1 and 2.

Illustrative Method of Manufacture

FIG. 1 is a flow diagram of an embodiment of a process of manufacture 100 of the composition.

As described above, the composition described herein includes at least one rehydration formulation and at least one target supplement, and may contain optional additional ingredients.

At step 102, the components of the rehydration formulation are combined.

In an embodiment, the rehydration formulation may include, but is not limited to, at least, about 9.0 to about 12.6 grams of glucose per liter solvent; about 12.9 grams to about 14.8 grams of sucrose per liter solvent; about 2.0 to 2.3 grams of sodium chloride per liter solvent; about 0.98 to about 1.5 grams of sodium citrate per liter solvent; about 1.4 to about 1.6 grams of potassium citrate per liter solvent; and about 0.50 to about 0.65 grams of dipotassium phosphate per liter solvent.

In another embodiment, the rehydration formulation may include, but is not limited to, at least, about 9.0 to about 10.8 grams of glucose per liter solvent; about 12.6 grams to about 15.7 grams of sucrose per liter solvent; about 2.2 to 2.5 grams of sodium chloride per liter solvent; about 0.68 to about 1.3 grams of sodium citrate per liter solvent; about 1.4 to about 1.6 grams of potassium citrate per liter solvent; and about 0.50 to about 0.65 grams of dipotassium phosphate per liter solvent.

In yet another embodiment, the rehydration formulation may include, but is not limited to, at least, about 14.0 to about 15.6 grams of dextrose per liter solvent; about 2.1 to about 2.5 sodium chloride per liter solvent, about 2.30 to about 2.76 grams of sodium citrate per liter solvent; and about 1.28 to about 1.88 grams of potassium chloride per liter solvent.

The solvent (e.g., water) may be included as part of the composition or may be added later upon preparation of a solution including the composition. The composition may be manufactured as one or more of a powder, a gel, an emulsion, or a liquid.

At step 104, at least one target supplement may be added to the at least one rehydration formula, as described above.

At step 106, optional additional ingredients may be added. Optional additional ingredients may include, but are not limited to, flavoring, preservatives, sweeteners, colorants, anti-caking agents, gelling agents, antimicrobials, citric acid, and/or excipients.

The target supplements and other ingredients may be added in variable quantities. However, when in solution, the osmolarity of glucose and osmolarity of sodium in the composition are each at least about 50 mmol/L and are maintained in an approximate ratio between each other of 1:1. In an example, the glucose and sodium in the composition have osmolarities of about 50 to about 80 mmol per liter, or about 60 to about 70 mmol/L, or about 75 to about 125 mmol/L. Additionally, the total osmolarity of the composition, when in solution, is about 210 mmol/L to about 260 mmol/L.

In another example, dextrose (glucose) in the composition has an osmolarity of about 70 to about 90 mmol per liter, or about 78 to about 84 mmol/L, or about 80 to about 82 mmol/L, and the sodium in the composition has an osmolarity of about 67.3 to about 69.3 mmol per liter, or about 60 to about 76 mmol/L, or about 55 to about 81 mmol/L. Additionally, the total osmolarity of the composition, when in solution, is about 200 mmol/L to about 310 mmol/L, or about 255 mmol/L to 275 mmol/L.

At step 108, the composition may be transformed into a desired state if not already in the desired state. For example, a composition in the form of a powder may be diluted with water to prepare it for consumption.

Illustrative Method of Use

FIG. 2 is a flow diagram of an embodiment of a method of use 200 of the composition as described above and in FIG. 1. In particular, FIG. 2 illustrates an embodiment in which the method of use comprises orally delivering a target supplement, in a composition, to a subject in need thereof.

At step 202, a subject may be identified who is in need of a target supplement.

At step 204, a composition is prepared that contains at least one rehydration formulation as described herein and at least one target supplement as described herein. Optional additional ingredients may also be added.

At step 206, the composition may be diluted with water if not already in solution. For example, when the composition is in the form of a powder, or a gel, or an emulsion, the method comprises dissolving the composition in a quantity of water that is at least sufficient to provide a solution wherein the at least one rehydration formulation and the at least one target supplement are substantially dissolved to be suitable for consumption by drinking and to ensure the molarity of the sodium and glucose are each at least about 50 mmol/L.

At step 208, the solution is orally ingested by the subject in need thereof.

EXAMPLES

Example 1: Plasma Levels of Target Supplements Melatonin and L-Theanine

A pharmacokinetic test was conducted to determine the absorption of melatonin and L-theanine in a Test Composition compared to a Reference Comparator product by obtaining plasma levels of melatonin and L-theanine at times after ingestion of each of the Test Composition and the Reference Comparator.

The objective of the test was to compare the pharmacokinetics profiles of the Test Composition with a label equivalent Reference Comparator.

The test enrolled a total of six healthy adult subjects, including three men and three women.

Preparation and Administration of Test Composition and Reference Comparator

Test subjects were instructed to fast for at least 4 hours prior to ingesting the study products and the initiation of each test period.

Subjects ingested a single dose of Test Composition on a first day, and ingested a single dose of the Reference Comparator on a second day that was a minimum of approximately 5 days of wash-out period later.

Both the Test Composition and Reference Comparator included 3 mg melatonin and 50 mg L-theanine. The Reference Comparator product used was Schiff Knockout® Tablets, a marketed melatonin-based supplement, manufactured and sold by Schiff. The Reference Comparator had the label equivalent for melatonin and L-theanine dosage as the Test Composition. The contents of the Reference Comparator were based on the supplement facts panel of Reference Comparator.

The ingredients listed in Table 3 formed a powder mixture. The mixture was combined with 8 fl. oz. (236.58 grams) of water to form the Test Composition. The resultant osmolarity of the ingredients is listed in Table 3. The resultant osmolarity of dextrose, sodium, chloride, potassium, and citrate in the Test Composition are listed in Table 4.

First, test subjects ingested the Test Composition. After completion of the test of Test Composition, a minimum of approximately 5 days of wash-out period was required before test subjects ingested the Reference Comparator.

Plasma levels of the target supplements melatonin and L-theanine in each of the subjects were measured at 15 minutes, 30 minutes, 60 minutes, 90 minutes, and 120 minutes after ingestion of the Test Composition/Reference Comparator.

Plasma Levels at 15 Minutes after Ingestion

Blood samples of each subject were collected within 1 hour prior to ingestion of the dose, and at approximately 15, 30, 60, 90 and 120 minutes after ingestion of the dose.

Table 5 (below) lists the plasma levels of each of melatonin (in picograms per milliliter) and L-theanine (in nanograms per milliliter), measured at 15 minutes after ingestion of each of the six subjects 1-6.

TABLE 5

Individual Plasma Levels at +15 Minutes Post-Ingestion

| Subject | Test Comp. Melatonin (pg/ml) | Ref. Comp. Melatonin (pg/ml) | Test Comp. L-thea (ng/ml) | Ref. Comp L-thea. (ng/ml) |
|---|---|---|---|---|
| 1 | 2108 | 145 | 209 | 0 |
| 2 | 446 | 390 | 320 | 163 |
| 3 | 743 | 188 | 1371 | 230 |
| 4 | 1999 | 2433 | 948 | 825 |
| 5 | 6382 | 654 | 746 | 36 |
| 6 | 8778 | 2145 | 1543 | 565 |

Table 5 illustrates that L-theanine plasma levels at 15 minutes after ingesting the Test Composition were greater than L-theanine plasma levels at 15 minutes after ingesting the Reference Comparator for all six subjects.

Additionally, Table 5 illustrates that melatonin plasma levels at 15 minutes after ingesting the Test Composition were greater than melatonin plasma levels at 15 minutes after ingesting the Reference Comparator for five of the six subjects.

TABLE 6

Mean Plasma Levels Change from Baseline at +15 Minutes Post-Ingestion

| Product | Melatonin (pg/ml) | L-theanine (ng/ml) |
|---|---|---|
| Test Comp. | 3384 | 851 |
| Ref. Comp. | 993 | 277 |

Table 6 is based on the data of Table 5 (above) and lists the mean change (across six subjects) in plasma levels from baseline of each of melatonin (in pg/ml) and L-theanine (in ng/ml) of the six subjects at 15 minutes after ingestion of the Test Composition on the first day and at 15 minutes after ingestion of Reference Comparator on the second day.

As shown in Table 6, the mean change from baseline of L-theanine plasma level 15 minutes after ingesting the Test Composition (851 ng/ml) was approximately 3.1 times greater than the mean change from baseline of L-theanine plasma level 15 minutes after ingesting the Reference Comparator (277 ng/ml).

Additionally, as also shown in Table 6, the mean change from baseline of melatonin plasma level measured 15 minutes after ingesting the Test Composition (3384 ng/ml) was approximately 3.4 times greater than the mean change from baseline of melatonin plasma level measured 15 minutes after ingesting the Reference Comparator (993 ng/ml).

Tables 5 and 6 illustrate that the target supplements melatonin and L-theanine are absorbed into the human body more quickly and in greater quantities (as measured at 15 minutes post-ingestion) when ingested as part of a composition as described herein (that is, the Test Composition, which includes the at least one target supplement and a rehydration formulation) than when ingested as part of the Reference Comparator.

Plasma Levels at 15, 30, 60, 90, and 120 Minutes after Ingestion

Table 7 shows the mean change in plasma levels (of all six subjects, from baseline) at each of 15, 30, 60, 90, and 120 minutes after ingestion of the Test Composition and Reference Comparator product.

TABLE 7

Mean Plasma Level Change from Baseline of Melatonin (pg/ml) and of L-Theanine (ng/ml) at 15, 30, 60, 90 and 120 Minutes Post-Ingestion

| | Test +15" | Ref +15" | Test +30" | Ref. +30" | Test +60" | Ref. +60" | Test +90" | Ref. +90" | Test +120" | Ref. +120" |
|---|---|---|---|---|---|---|---|---|---|---|
| Mela. | 3384 | 993 | 5173 | 5723 | 3163 | 4547 | 1919 | 2896 | 1075 | 1921 |
| L-thea. | 851 | 277 | 2242 | 1732 | 2089 | 2942 | 1464 | 2176 | 1023 | 1609 |

Table 7 illustrates that the mean L-theanine plasma level peaked earlier when included as part of the Test Composition than when included as part of the Reference Comparator. That is, the highest mean plasma level of L-theanine when included in the Test Composition was at 30 minutes post-ingestion (2,242 ng/ml), while the highest mean plasma level of L-theanine when included in the Reference Comparator was at 60 minutes post-ingestion (2,942 ng/ml). Table 7 also illustrates that the difference between the Test Composition and the Reference Comparator in the speed of absorption of melatonin peaked at 15 minutes after ingestion (3,384 and 993 pg/ml, respectively).

Summary of Example 1

Example 1 provides evidentiary support that there is enhanced absorption (greater amount and faster) of melatonin and L-theanine (measured at 15 minutes after ingestion) when included with the composition described than without being included in the composition. Example 1 also illustrates that L-theanine mean plasma level peaks earlier when part of the Test Composition than when part of the Reference Comparator.

Example Clauses

1. A composition comprising:
at least one target supplement having a first absorption rate and a first absorption amount; and
at least one rehydration formulation,
wherein, when the at least one target supplement is ingested as part of the composition, the at least one target supplement has at least one of a second absorption rate that is greater than the first absorption rate, or a second absorption amount that is greater than the first absorption amount.

2. The composition of clause 1, wherein the composition is a powder, a gel, an emulsion, or a liquid.

3. The composition of clause 1, wherein the at least one target supplement targets a condition of a subject.

4. The composition of clause 3, wherein the condition is vitamin deficiency, and wherein the at least one target supplement includes at least one of vitamin C, vitamin $B_3$, vitamin $B_5$, vitamin $B_6$, or vitamin $B_{12}$.

5. The composition of clause 3, wherein the condition is sleeplessness, and wherein the at least one target supplement includes at least one of melatonin, L-theanine, valerian root, 5-hydroxytryptophan, or passionflower.

6. The composition of clause 3, wherein the condition is post-exercise fatigue, and wherein the at least one target supplement includes at least one of whey protein, soy protein, branched chain amino acids, glutamine, beta-alanine, or creatine.

7. The composition of clause 3, wherein the condition is anticipated post-exercise fatigue, and wherein the at least one target supplement includes at least caffeine, branched chain amino acids, and beta-alanine.

8. The composition of clause 1, wherein the second absorption rate is between two and six times faster than the first absorption rate.

9. The composition of clause 1, wherein the first absorption rate and the second absorption rate comprise absorption rates in the ileum, and wherein the second absorption rate is between two and three times faster than the first absorption rate.

10. The composition of clause 1, wherein the first absorption rate and the second absorption rate comprise absorption rates in the jejunum, and wherein the second absorption rate is between four and six times faster than the first absorption rate.

11. The composition of clause 1, wherein the at least one rehydration formulation includes at least:
about 9.0 to about 12.6 grams of glucose per liter solvent;
about 12.9 to about 14.8 grams of sucrose per liter solvent;
about 2.0 to about 2.3 grams of sodium chloride per liter solvent;
about 0.98 to about 1.5 grams of sodium citrate per liter solvent;
about 1.4 to about 1.6 grams of potassium citrate per liter solvent; and
about 0.50 to about 0.65 grams of dipotassium phosphate per liter solvent.

12. The composition of claim 1, wherein the at least one rehydration formulation includes at least:
about 9.0 to about 10.8 grams of glucose per liter solvent;
about 12.6 to about 15.7 grams of sucrose per liter solvent;
about 2.0 to about 2.5 grams of sodium chloride per liter solvent;
about 0.68 to about 1.3 grams of sodium citrate per liter solvent;
about 1.4 to about 1.6 grams of potassium citrate per liter solvent; and
about 0.50 to about 0.65 grams of dipotassium phosphate per liter solvent.

13. The composition of clause 1, wherein the composition has a total osmolarity of about 210 mmol/L to about 260 mmol/L.

14. The composition of clause 1, wherein the osmolarity of sodium in the composition is at least 50 mmol/L, and wherein the osmolarity of the glucose is at least 50 mmol/L.

15. A method for making a composition comprising mixing at least one rehydration formulation and at least one target supplement, the at least one target supplement having a first absorption rate and a first absorption amount,
wherein, when the target supplement is ingested as part of the composition, the at least one target supplement has at least one of a second absorption rate that is greater than the first absorption rate, or a second absorption amount that is greater than the first absorption amount.

16. The method of clause 15, wherein the composition is a powder, a gel, an emulsion, or a liquid.

17. The method of clause 16, wherein the composition is a powder, and wherein the method further comprises dissolving the composition in a quantity of water that is at least sufficient to provide a solution such that the rehydration formulation and the at least one target supplement are substantially dissolved to be suitable for consumption by drinking.

18. The method of clause 15, wherein the at least one target supplement targets a condition of a subject.

19. The method of clause 18, wherein the condition is sleeplessness, and wherein the at least one target supplement includes at least one of: melatonin, 5-hydroxytryptophan, valerian root, L-theanine, or passionflower.

20. The method of clause 18, wherein the condition is anticipated post-exercise fatigue, and wherein the at least one target supplement includes at least caffeine, branched chain amino acids, and beta-alanine.

21. The method of clause 18, wherein the condition is post-exercise fatigue, and wherein the at least one target supplement includes at least whey protein, soy protein, branched chain amino acids, glutamine, beta-alanine, and creatine.

22. The method of clause 15, wherein the at least one rehydration formulation includes at least:
about 9.0 to about 12.6 grams of glucose per liter solvent;
about 12.9 to about 14.8 grams of sucrose per liter solvent;
about 2.0 to about 2.3 grams of sodium chloride per liter solvent;
about 0.98 to about 1.5 grams of sodium citrate per liter solvent;

about 1.4 to about 1.6 grams of potassium citrate per liter solvent; and about 0.50 to about 0.65 grams of dipotassium phosphate per liter solvent.

23. The method of clause 15, wherein the at least one rehydration formulation includes at least:

about 9.0 to about 10.8 grams of glucose per liter solvent;

about 12.6 to about 15.7 grams of sucrose per liter solvent;

about 2.0 to about 2.5 grams of sodium chloride per liter solvent;

about 0.68 to about 1.3 grams of sodium citrate per liter solvent;

about 1.4 to about 1.6 grams of potassium citrate per liter solvent; and about 0.50 to about 0.65 grams of dipotassium phosphate per liter solvent.

24. The method of clause 15, wherein the composition has a total osmolarity of about 210 mmol/L to about 260 mmol/L.

25. A method of orally delivering a target supplement to a subject in need thereof, comprising:

administering a composition to the subject, the composition including:

at least one target supplement having a first absorption rate and a first absorption amount; and at least one rehydration formulation, wherein, when the target supplement is ingested as part of the composition, the at least one target supplement has at least one of a second absorption rate that is greater than the first absorption rate, or a second absorption amount that is greater than the first absorption amount.

26. The method of clause 25, wherein the composition is a powder, a gel, an emulsion, or a liquid.

27. The method of clause 26, wherein the composition is a powder, and wherein the method further comprises dissolving the composition in a quantity of water that is at least sufficient to provide a solution such that the at least one rehydration formulation and the at least one target supplement are substantially dissolved to be suitable for consumption by drinking.

28. The method of clause 25, wherein the at least one target supplement targets a condition of a subject.

29. The method of clause 28, wherein the condition is sleeplessness, and wherein the at least one target supplement includes at least one of melatonin, 5-hydroxytryptophan, valerian root, L-theanine, or passionflower.

30. The method of clause 28, wherein the condition is anticipated post-exercise fatigue, and wherein the at least one target supplement includes at least caffeine, branched chain amino acids, and beta-alanine.

31. The method of clause 20, wherein the condition is post-exercise fatigue, and wherein the at least one target supplement includes at least whey protein, soy protein, branched chain amino acids, glutamine, beta-alanine, and creatine.

32. The method of clause 25, wherein the at least one rehydration formulation includes at least:

about 9.0 to about 12.6 grams of glucose per liter solvent;

about 12.9 to about 14.8 grams of sucrose per liter solvent;

about 2.0 to about 2.3 grams of sodium chloride per liter solvent;

about 0.98 to about 1.5 grams of sodium citrate per liter solvent;

about 1.4 to about 1.6 grams of potassium citrate per liter solvent; and about 0.50 to about 0.65 grams of dipotassium phosphate per liter solvent.

33. The method of clause 25, wherein the at least one rehydration formulation includes at least:

about 9.0 to about 10.8 grams of glucose per liter solvent;

about 12.6 to about 15.7 grams of sucrose per liter solvent;

about 2.0 to about 2.5 grams of sodium chloride per liter solvent;

about 0.68 to about 1.3 grams of sodium citrate per liter solvent;

about 1.4 to about 1.6 grams of potassium citrate per liter solvent; and about 0.50 to about 0.65 grams of dipotassium phosphate per liter solvent.

34. The method of clause 25, wherein the composition has a total osmolarity of about 210 mmol/L to 260 mmol/L.

35. A composition comprising:

at least one target supplement having a first bioavailability value; and at least one rehydration formulation, wherein, when the target supplement is ingested as part of the composition, the at least one target supplement has a second bioavailability value that is higher than the first bioavailability value.

36. The composition of clause 35, wherein the composition further comprises at least one of a flavor, a sweetener, a colorant, a preservative, an excipient, an anti-caking agent, a gelling agent, citric acid, or an antimicrobial.

37. The composition of clause 35, wherein at least one of:

the first bioavailability value and the second bioavailability value are based on at least the rate of absorption of the target supplement, or the first bioavailability value and the second bioavailability value are based on at least the amount of absorption of the target supplement.

38. The composition of clause 1, wherein the at least one rehydration formulation includes at least:

about 14.0 to about 15.6 grams of dextrose per liter solvent;

about 2.1 to about 2.5 grams of sodium chloride per liter solvent;

about 2.30 to about 2.76 grams of sodium citrate per liter solvent;

about 1.28 to about 1.88 grams of potassium chloride per liter solvent.

39. The composition of clause 1, wherein the composition has a total osmolarity of about 200 mmol/L to about 310 mmol/L.

40. The composition of clause 1, wherein the composition has a total osmolarity of about 255 mmol/L to about 275 mmol/L.

41. The method of clause 15, wherein the at least one rehydration formulation includes at least:

about 14.0 to about 15.6 grams of dextrose per liter solvent;

about 2.1 to about 2.5 grams of sodium chloride per liter solvent;

about 2.30 to about 2.76 grams of sodium citrate per liter solvent;

about 1.28 to about 1.88 grams of potassium chloride per liter solvent.

42. The method of clause 15, wherein the composition has a total osmolarity of about 200 mmol/L to about 310 mmol/L.

43. The method of clause 15, wherein the composition has a total osmolarity of about 255 mmol/L to about 275 mmol/L.

44. The method of clause 25, wherein the at least one rehydration formulation includes at least:
   about 14.0 to about 15.6 grams of dextrose per liter solvent;
   about 2.1 to about 2.5 grams of sodium chloride per liter solvent;
   about 2.30 to about 2.76 grams of sodium citrate per liter solvent;
   about 1.28 to about 1.88 grams of potassium chloride per liter solvent.

45. The method of clause 25, wherein the composition has a total osmolarity of about 200 mmol/L to about 310 mmol/L.

46. The method of clause 25, wherein the composition has a total osmolarity of about 255 mmol/L to about 275 mmol/L.

47. The composition of clause 3, wherein the condition is low energy, and wherein the at least one target supplement includes at least one of yerba mate, a vitamin, caffeine, coffee beans, green coffee extract, matcha green tea, black tea, white tea, ginseng, ashwagandha, or theobromine.

CONCLUSION

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

One skilled in the art will realize that a virtually unlimited number of variations to the above descriptions are possible, and that the examples and the accompanying figures are merely to illustrate one or more embodiments or examples of implementations.

It will be understood by those skilled in the art that various other modifications can be made, and equivalents can be substituted, without departing from claimed subject matter. Additionally, many modifications can be made to adapt a particular situation to the teachings of claimed subject matter without departing from the central concept described herein. Therefore, it is intended that claimed subject matter not be limited to the particular embodiments disclosed, but that such claimed subject matter can also include all embodiments falling within the scope of the appended claims, and equivalents thereof.

In the detailed description above, numerous specific details are set forth to provide a thorough understanding of claimed subject matter. However, it will be understood by those skilled in the art that claimed subject matter can be practiced without these specific details. In other instances, methods, apparatuses, or systems that would be known by one of ordinary skill have not been described in detail so as not to obscure claimed subject matter.

Reference throughout this specification to "one embodiment" or "an embodiment" can mean that a particular feature, structure, or characteristic described in connection with a particular embodiment can be included in at least one embodiment of claimed subject matter. Thus, appearances of the phrase "in one embodiment" or "an embodiment" in various places throughout this specification are not necessarily intended to refer to the same embodiment or to any one particular embodiment described. Furthermore, it is to be understood that particular features, structures, or characteristics described can be combined in various ways in one or more embodiments. In general, of course, these and other issues can vary with the particular context of usage. Therefore, the particular context of the description or the usage of these terms can provide helpful guidance regarding inferences to be drawn for that context.

Conditional language such as, among others, "can," "could," "might" or "may," unless specifically stated otherwise, are understood within the context to present that certain examples or embodiments include, while other examples or embodiments do not include, certain features, elements and/or steps. Thus, such conditional language is not generally intended to imply that certain features, elements and/or steps are in any way required for one or more examples or embodiments or that one or more examples or embodiments necessarily include logic for deciding, with or without user input or prompting, whether certain features, elements and/or steps are included or are to be performed in any particular example or embodiment. Conjunctive language such as the phrase "at least one of X, Y or Z," unless specifically stated otherwise, is to be understood to present that an item, term, etc., can be either X, Y, or Z, or a combination thereof.

What is claimed is:

1. A composition comprising:
   at least one target supplement having a first absorption rate when ingested separately from the composition, wherein the at least one target supplement comprises at least one of melatonin or L-theanine; and
   at least one rehydration formulation comprising sodium, chloride, glucose-containing saccharide, potassium, and citrate, and wherein the glucose osmolarity is greater than the sodium osmolarity in the composition,
   wherein, when the at least one target supplement is ingested as part of the composition, the at least one target supplement has a second absorption rate measured less than 30 minutes after ingestion that is greater than the first absorption rate.

2. The composition of claim 1, wherein the at least one target supplement targets a condition of a subject.

3. The composition of claim 2, wherein the condition is sleeplessness, and wherein the composition further comprises at least one of valerian root, 5-hydroxytryptophan, or passionflower, or comprises both melatonin and L-theanine.

4. The composition of claim 1, wherein the second absorption rate is between two and six times faster than the first absorption rate.

5. The composition of claim 1, wherein the at least one rehydration formulation includes at least:
   about 9.0 to about 12.6 grams of glucose per liter solvent;
   about 12.9 to about 14.8 grams of sucrose per liter solvent;
   about 2.0 to about 2.3 grams of sodium chloride per liter solvent;
   about 0.98 to about 1.5 grams of sodium citrate per liter solvent;
   about 1.4 to about 1.6 grams of potassium citrate per liter solvent; and
   about 0.50 to about 0.65 grams of dipotassium phosphate per liter solvent.

6. The composition of claim 1, wherein the at least one rehydration formulation includes at least:
   about 9.0 to about 10.8 grams of glucose per liter solvent;
   about 12.6 to about 15.7 grams of sucrose per liter solvent;
   about 2.0 to about 2.5 grams of sodium chloride per liter solvent;

about 0.68 to about 1.3 grams of sodium citrate per liter solvent;
about 1.4 to about 1.6 grams of potassium citrate per liter solvent; and
about 0.50 to about 0.65 grams of dipotassium phosphate per liter solvent.

7. The composition of claim 1, wherein the osmolarity of sodium in the composition is at least 50 mmol/L, and wherein the osmolarity of the glucose is at least 50 mmol/L.

8. The composition of claim 1, wherein the at least one rehydration formulation includes at least:
about 14.0 to about 15.6 grams of dextrose per liter solvent;
about 2.1 to about 2.5 grams of sodium chloride per liter solvent;
about 2.30 to about 2.76 grams of sodium citrate per liter solvent;
about 1.28 to about 1.88 grams of potassium chloride per liter solvent.

9. The composition of claim 1, wherein the composition has a total osmolarity of about 200 mmol/L to about 310 mmol/L.

10. The composition of claim 1, wherein the composition has a total osmolarity of about 255 mmol/L to about 275 mmol/L.

11. A method for making the composition of claim 1, comprising mixing the at least one rehydration formulation and the at least one target supplement.

12. The method of claim 11, wherein the at least one target supplement targets a condition of a subject.

13. The method of claim 12, wherein the condition is sleeplessness, and wherein the composition further comprises at least one of: 5-hydroxytryptophan, valerian root, or passionflower, or comprises both melatonin and L-theanine.

14. The method of claim 11, wherein the at least one rehydration formulation includes at least:
about 9.0 to about 12.6 grams of glucose per liter solvent;
about 12.9 to about 14.8 grams of sucrose per liter solvent;
about 2.0 to about 2.3 grams of sodium chloride per liter solvent;
about 0.98 to about 1.5 grams of sodium citrate per liter solvent;
about 1.4 to about 1.6 grams of potassium citrate per liter solvent; and
about 0.50 to about 0.65 grams of dipotassium phosphate per liter solvent.

15. The method of claim 11, wherein the at least one rehydration formulation includes at least:
about 9.0 to about 10.8 grams of glucose per liter solvent;
about 12.6 to about 15.7 grams of sucrose per liter solvent;
about 2.0 to about 2.5 grams of sodium chloride per liter solvent;
about 0.68 to about 1.3 grams of sodium citrate per liter solvent;
about 1.4 to about 1.6 grams of potassium citrate per liter solvent; and
about 0.50 to about 0.65 grams of dipotassium phosphate per liter solvent.

16. The method of claim 11, wherein the at least one rehydration formulation includes at least:
about 14.0 to about 15.6 grams of dextrose per liter solvent;
about 2.1 to about 2.5 grams of sodium chloride per liter solvent;
about 2.30 to about 2.76 grams of sodium citrate per liter solvent;
about 1.28 to about 1.88 grams of potassium chloride per liter solvent.

17. A method of orally delivering a target supplement to a subject in need thereof, comprising:
administering to the subject the composition of claim 1.

18. The method of claim 17, wherein the at least one target supplement targets a condition of a subject.

19. The method of claim 18, wherein the condition is sleeplessness, and wherein the composition further comprises at least one of 5-hydroxytryptophan, valerian root, or passionflower, or comprises both melatonin and L-theanine.

20. The method of claim 17, wherein the at least one rehydration formulation includes at least:
about 9.0 to about 12.6 grams of glucose per liter solvent;
about 12.9 to about 14.8 grams of sucrose per liter solvent;
about 2.0 to about 2.3 grams of sodium chloride per liter solvent;
about 0.98 to about 1.5 grams of sodium citrate per liter solvent;
about 1.4 to about 1.6 grams of potassium citrate per liter solvent; and
about 0.50 to about 0.65 grams of dipotassium phosphate per liter solvent.

21. The method of claim 17, wherein the at least one rehydration formulation includes at least:
about 9.0 to about 10.8 grams of glucose per liter solvent;
about 12.6 to about 15.7 grams of sucrose per liter solvent;
about 2.0 to about 2.5 grams of sodium chloride per liter solvent;
about 0.68 to about 1.3 grams of sodium citrate per liter solvent;
about 1.4 to about 1.6 grams of potassium citrate per liter solvent; and
about 0.50 to about 0.65 grams of dipotassium phosphate per liter solvent.

22. The method of claim 17, wherein the at least one rehydration formulation includes at least:
about 14.0 to about 15.6 grams of dextrose per liter solvent;
about 2.1 to about 2.5 grams of sodium chloride per liter solvent;
about 2.30 to about 2.76 grams of sodium citrate per liter solvent;
about 1.28 to about 1.88 grams of potassium chloride per liter solvent.

* * * * *